United States Patent [19]

Dorn

[11] Patent Number: 4,605,656

[45] Date of Patent: Aug. 12, 1986

[54] PYRIDINE AND PYRAZINE OXIME COMPOUNDS AS FUNGICIDES

[75] Inventor: Franz Dorn, Dielsdorf, Switzerland

[73] Assignee: Hoffmann-La Roche Inc., Nutley, N.J.

[21] Appl. No.: 736,061

[22] Filed: Oct. 21, 1983

Related U.S. Application Data

[63] Continuation of Ser. No. 307,395, Oct. 1, 1981, abandoned.

[30] Foreign Application Priority Data

Oct. 10, 1980 [CH] Switzerland .......................... 7584/80
Jul. 15, 1981 [CH] Switzerland .......................... 4642/81

[51] Int. Cl.⁴ ................. C07D 213/53; C07D 241/12; A01N 35/04; A01N 35/10
[52] U.S. Cl. ................................... 514/255; 514/277; 546/338; 544/336
[58] Field of Search .................. 546/338; 544/336; 514/255, 277

[56] References Cited

U.S. PATENT DOCUMENTS

| | | | |
|---|---|---|---|
| 3,167,563 | 1/1965 | Schumann | 548/338 |
| 3,205,234 | 9/1965 | Schumann | 548/338 |
| 4,244,959 | 1/1981 | Freenor | 548/334 |
| 4,263,305 | 4/1981 | Epstein | 548/338 |
| 4,305,947 | 12/1981 | Bartner | 548/338 |
| 4,352,804 | 10/1982 | Van Zorge | 514/252 |

FOREIGN PATENT DOCUMENTS

| | | | |
|---|---|---|---|
| 7678 | 2/1980 | European Pat. Off. | 544/336 |
| 7679 | 2/1980 | European Pat. Off. | 544/336 |
| 2723942 | 7/1978 | Fed. Rep. of Germany | 544/336 |
| 2015524 | 9/1979 | United Kingdom | 544/336 |

OTHER PUBLICATIONS

Kempf, ". . . Determination of Iron . . . with 2-pyridyl ketoxime . . . ," *Chem. Abst.* 67:111292(z) (1967).
Franchetti, et al., "Structural Activity . . . Hydroxyimino 1-pyridyl-2-phenylethanes," *Chem. Abst.* 71:77621(b) (1969).
Malone, Diana, "Transition Metal Complexes Syn--phenyl-2-pyridyl ketoxime," *Chem. Abst.* 79:61001(d) (1973).
Bhaskare, et al., "Determination of CuII with Syn--phenyl-α-pyridyl ketoneoxime . . . ", *Chem. Abst.* 83:169138(a) 1975.
Case, et al., "Synthesis and Chelation Properties of Oximes," *J. Heterocyclic Chem.* 77:(vol. 14) pp. 1–5.
Niemers, et al., "Pyridylalkyl-subtituierte Amine", *Synthesis* (1976) pp. 593–595.
Ciba, Ltd., "Oxime Ethers," *Chem. Abst.* 66:28501(a) (1967).
Kato, et al., ". . . Benzoyl Pyrimidine Oximes . . . ," *Chem. Abst.* 66:85680(g) (1967).
Tanaka, et al., "Pyridyl Ketoneoxime Ethers," *Chem. Abst.* 90:103840n (1979).

*Primary Examiner*—Donald G. Daus
*Assistant Examiner*—G. Hendricks
*Attorney, Agent, or Firm*—Jon S. Saxe; George M. Gould; William H. Epstein

[57] ABSTRACT

Pyridine and pyrazine compounds of the formula

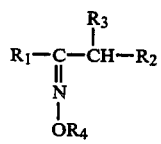

I wherein $R_1$, $R_2$, $R_3$ and $R_4$ are as hereinafter set forth and acid addition salts of these compounds, processes for their preparation, fungicidal compositions containing these compounds as the active ingredients and methods for the use of such compounds or compositions for combating fungi in agriculture and horticulture are disclosed.

10 Claims, No Drawings

PYRIDINE AND PYRAZINE OXIME COMPOUNDS AS FUNGICIDES

This is a continuation of application Ser. No. 307,395 filed Oct. 1, 1981, now abandoned.

SUMMARY OF THE INVENTION

This invention relates to compounds of the formula

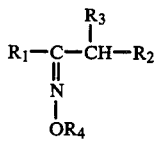

wherein $R_1$ is 2-halo, 4-halo- or 2,4-dihalophenyl, $R_2$ is 3-pyridyl or 2-pyrazinyl, $R_3$ is hydrogen or straight-chain $C_{1-4}$-alkyl, and $R_4$ is $C_{1-6}$-alkyl, $C_{3-6}$-cycloalkyl, $C_{3-6}$-alkenyl or $C_{3-6}$-alkynyl, and acid addition salts of these compounds.

This invention also relates to a process for the preparation of such compounds, to fungicidal compositions containing these compounds as the active ingredients and to methods for the use of such compounds or compositions in combating fungi in agriculture and horticulture.

DETAILED DESCRIPTION OF THE INVENTION

The pyridine and pyrazine compounds of this invention are characterized by the following formula

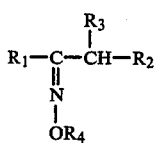

wherein $R_1$ is 2-halo-, 4-halo- or 2,4-dihalo-phenyl, $R_2$ is 3-pyridyl or 2-pyrazinyl, $R_3$ is hydrogen or straight-chain $C_{1-4}$-alkyl, and $R_4$ is $C_{1-6}$-alkyl, $C_{3-6}$-cycloalkyl, $C_{3-6}$-alkenyl or $C_{3-6}$-alkynyl, and acid addition salts thereof.

The compounds of formula I possess fungicidal properties and are suitable as fungicidal agents.

The invention is also directed to a process for the preparation of the compounds of formula I and their acid addition salts, to fungicidal compositions which contain the compounds of formula I as the active ingredient and to methods for the use of the compounds or fungicidal compositions for combating fungi in agriculture and horticulture.

As used herein the term "halo" denotes fluoro, chloro, bromo and iodo. The preferred halo atom is chloro.

The halogen atoms in a 2,4-dihalo-phenyl group denoted by $R_1$ can be the same or different.

The terms "$C_{1-6}$-alkyl", "$C_{3-6}$-alkenyl" and "$C_{3-6}$-alkynyl" denote not only straight-chain but also branched-chain hydrocarbon groups. Examples of alkyl groups within the scope of the compounds of formula I are methyl, ethyl, n-propyl, isopropyl, n-butyl, tert-butyl, isoamyl and n-hexyl.

When $R_4$ is $C_{1-6}$-alkyl, $C_{3-6}$-alkenyl or $C_{3-6}$-alkynyl, then the preferred groups are $C_{1-4}$-alkyl, $C_3$- or $C_4$-alkenyl or $C_3$- or $C_4$-alkynyl respectively. The allyl group is an especially preferred alkenyl group and the propargyl group is an especially preferred alkynyl group.

$R_1$ preferably is 4-chlorophenyl or 2,4-dichlorophenyl, especially the latter group.

$R_3$ preferably is hydrogen, methyl or ethyl, especially hydrogen.

Examples of compounds of formula I are:
4'-chloro-2-(3-pyridyl)-acetophenone O-allyl oxime, and
2',4'-dichloro-2-(2-pyrazinyl)-acetophenone O-isopropyl oxime.

A particularly preferred compound of formula I is 2',4'-dichloro-2-(3-pyridyl)-acetophenone O-methyl oxime.

Since the compounds of formula I contain a C=N double bond, geometric isomerism occurs in these compounds. In addition, asymmetric carbon atoms can be present and, therefore, the compounds can exist as optical antipodes. Formula I is, therefore, intended to include all of these possible isomeric forms.

The acid addition salts of the compounds of formula I are physiologically compatible salts. These salts are preferably salts of the compounds of formula I with inorganic or organic acids such as hydrochloric acid, nitric acid, phosphoric acid, mono- and bifunctional carboxylic acids and hydroxycarboxylic acids, e.g., acetic acid, maleic acid, succinic acid, fumaric acid, tartaric acid, citric acid, salicylic acid, sorbic acid and lactic acid, and sulfonic acid, e.g., 1,5-naphthalenedisulfonic acid.

The compounds of formula I and their salts are prepared by the procedures detailed below.

Procedure A

Reacting an oxime of the formula

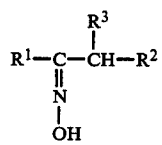

wherein $R_1$, $R_2$ and $R_3$ are as previously described with a compound of the formula $$R_4U \qquad \text{III}$$

wherein $R_4$ is as previously described and U is a leaving group, e.g., chlorine, bromine, iodine, mesyloxy, tosyloxy or an alkylsulfate group.

A starting material of formula II is reacted with a compound of formula III conveniently in an organic solvent and in the presence of a base. Reaction temperatures can range from about 0° C. to the reflux temperature of the reaction mixture. The solvent can be protic or non-protic. When protic solvents such as, for example, alcohols, preferably methanol or ethanol, are used, an alkali metal hydroxide, e.g., sodium or potassium hydroxide, or an alkali metal alcoholate is preferably used as the base. When non-protic solvents such as, for example, ethers or ether-like compounds, preferably tetrahydrofuran or dimethoxyethane, and dialkylamides, preferably dimethylformamide, are used, an alkali metal hydride, e.g., sodium hydride, is preferably used as the base.

In a preferred embodiment of procedure A, sodium hydride is used as the base and an ether or an ether-like compound, especially tetrahydrofuran or dimethoxyethane, or a dialkylamide, especially dimethylformamide, is used as the solvent.

Procedure B

Reacting a ketone of the formula

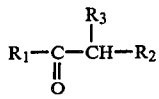

wherein $R_1$, $R_2$ and $R_3$ are as previously described with a O-substituted hydroxylamine of the formula

wherein $R_{41}$ is $C_{1-6}$-alkyl, $C_{3-6}$-cycloalkyl or $C_{3-6}$-alkenyl.

Procedure B yields compounds of formula I wherein $R_4$ is $C_{1-6}$-alkyl, $C_{3-6}$-cycloalkyl or $C_{3-6}$-alkenyl. The reaction is conveniently carried out in an organic solvent, for example an alcohol such as methanol or ethanol, a dialkylamide such as dimethylformamide or a tertiary amine such as pyridine. The reaction is preferably carried out in a temperature range between room temperature and the reflux temperature of the reaction mixture. Since the starting material of formula V is preferably used in the form of an acid addition salt, e.g., the hydrochloride or hydrosulfate, a base such as sodium or potassium carbonate, triethylamine or pyridine is conveniently added to the reaction mixture.

If desired, a compound of formula I obtained as described above may be converted into an acid addition salt.

For the preparation of acid addition salts, the compounds of formula I can be reacted with inorganic or organic acids such as, for example, hydrochloric acid, nitric acid, phosphoric acid, mono- and bifunctional carboxylic acids and hydroxycarboxylic acids or sulfonic acids.

Isolation and purification of the compounds of formula I and their acid addition salts is carried out according to conventional procedures.

The compounds of formulae II, III, IV and V used as the starting materials are either known or can be prepared according to known methods. For example, the oximes of formula II can be prepared from the corresponding ketones of formula IV by reaction with hydroxylamine, and the ketones themselves can be prepared in accordance with the processes described in DOS No. 2 221 546, DOS No. 2 800 010 and British Patent Specification No. 2 015 524.

The compounds of formula I and their acid addition salts have fungicidal activity and are useful in controlling fungi in agriculture and in horticulture. They are especially suitable for eradicating or checking phytopathogenic fungi on parts of plants, e.g., leaves, stems, roots, tubers, fruits or flowers, on seeds and in the soil. The compounds are especially effective in the control of powdery mildew fungi such as, for example, *Erysiphe graminis* (powdery mildew of cereals), *Erysiphe cichoracearum* (powdery mildew of cucumbers), *Podosphaera leucotricha* (powdery mildew of apples) and *Sphaerotheca pannosa* (powdery mildew of roses); of *Venturia inaequalis* (apple scab); and of rust fungi such as, for example, those of the genera Puccinia, Uromyces and Hemileia, especially *Puccinia coronata* (crown rust of oats), *Puccinia recondita* (leaf rust of cereals), *Uromyces appendiculatus* (bean rust) and *Hemileia vastatrix* (coffee rust).

Further, various compounds of formula I of this invention are also active against phytopathogenic fungi of the following genera: Helminthosporium, Rhizoctonia, Septoria, Cercospora, Corticium, Tilletia and Ustilago.

Moreover, individual compounds of formula I of this invention have a pronounced activity against wood-destroying fungi such as, for example, *Coniophora puteana* and *Lenzites trabea*. Moreover, individual compounds are also active against phytopathogenic bacteria such as, for example, *Xanthomonas oryzae*.

The compounds of formula I of this invention also have systemic activity and have good plant tolerance.

The compounds of formula I are active under greenhouse conditions at a concentration of 5 mg to 500 mg of active ingredient (i.e., compound of formula I) per liter of spray liquor. In the open air, they are advantageously applied in concentrations of 50 g to 1000 g of active ingredient per hectare and treatment. For example, to successfully control apple mildew and apple scab, concentrations of 50 g to 400 g of active ingredient per hectare and application are used. For control of seedborne fungi in a disinfecting process, the compounds of formula I are advantageously applied in concentrations of 0.1 g to 2.5 g of active ingredient per kg of seeds.

This invention is also directed to plant fungicidal compositions comprising compatible inert carrier material and, as the active ingredient, one or more of the compounds of formula I. These compositions can be, for example, spray liquors, aqueous suspensions, emulsions, emulsifiable concentrates and powders. Depending on its type, a plant fungicidal composition of this invention contains from about 0.0001 percent to about 95 percent by weight, based on the weight of the total composition, of a compound or compounds of formula I as the active ingredient.

Examples of compatible inert carrier material include inert pulverous carrier materials such as, for example, kaolin, bentonite, talc, whiting, magnesium carbonate and siliceous earth; wetting or emulsifying agents and inert solvents.

For the preparation of pulverous fungicidal compositions, the inert pulverous carrier material can be admixed with the active ingredients (e.g., by grinding them together). In an alternate procedure, the inert pulverous carrier materials can be impregnated with a solution of the active ingredient with the solvent subsequently removed by evaporation, heating or aspiration under reduced pressure.

These powder compositions can be applied to plants to be protected in the form of dusts using standard apparatus. By the addition of wetting and/or dispersing agents to the pulverous fungicidal compositions, the compositions are readily wettable with water and, thus, can be used as aqueous suspensions suitable for spray applications.

To prepare emulsifiable concentrates, the active ingredients can be mixed with an emulsifying agent or dissolved in an inert solvent and mixed with an emulsifier. Ready-for-use emulsions are prepared by dilution of such concentrates with water. These concentrates can contain from about 5 percent to about 95 percent by weight and, preferably, from about 25 percent to about 75 percent by weight, based on the total weight of the concentrate, of active ingredient.

The fungicidal compositions of this invention can contain, in addition to the compounds of formula I, other active ingredients (e.g., other fungicidal agents, insecticidal and acaricidal agents, bactericides, plant growth regulators, fertilizers and the like). Such combination compositions are useful either for broadening the spectrum of activity or for specifically influencing the plant growth.

The compositions in accordance with the invention can be used in accordance with application methods which are conventional in plant protection or agriculture. The method in accordance with the invention for the control of fungi is characterized by treating the goods to be protected, e.g., plants, parts of plants or seeds, with an effective amount of a compound of formula I or a salt thereof or a composition of this invention.

The following Examples illustrate the invention. All temperatures are given in °C.

I. PREPARATION OF THE ACTIVE INGREDIENTS

Example 1

A solution of 13.3 g of 2',4'-dichloro-2-(3-pyridyl)-acetophenone in 40 ml of ethanol is treated with 10 g of sodium carbonate and 8.3 g of O-methylhydroxylamine hydrochloride; the mixture is subsequently heated at reflux temperature while stirring. After 4 hours, the mixture is poured onto ice and extracted with ethyl acetate. The organic phase is washed, dried over sodium sulfate and concentrated under reduced pressure to yield 2',4'-dichloro-2-(3-pyridyl)-acetophenone O-methyl oxime as the E,Z-isomer mixture in the form of a yellowish oil. Chromatographic separation on silica gel with n-hexane/ethyl acetate (4:1) as the eluant yields firstly the E-isomer ($n_D^{20}=1.5845$) and then the Z-isomer ($n_D^{20}=1.5745$).

In an analogous manner,
from 4'-chloro-2-(3-pyridyl)-acetophenone and O-methylhydroxylamine hydrochloride there is obtained 4'-chloro-2-(3-pyridyl)-acetophenone O-methyl oxime, m.p. 55°–58°;
from 4'-chloro-2-(2-pyrazinyl)-acetophenone and O-methylhydroxylamine hydrochloride there is obtained 4'-chloro-2-(2-pyrazinyl)-acetophenone O-methyl oxime, m.p. 53°–58°;
from 4'-chloro-2-(2-pyrazinyl)-acetophenone and O-ethylhydroxylamine hydrochloride there is obtained 4'-chloro-2-(2-pyrazinyl)-acetophenone O-ethyl oxime, m.p. 44°–46°;
from 4'-chloro-2-(2-pyrazinyl)-acetophenone and O-allylhydroxylamine hydrochloride there is obtained 4'-chloro-2-(2-pyrazinyl)-acetophenone O-allyl oxime as a yellowish oil,
from 2',4'-dichloro-2-(3-pyridyl)-acetophenone and O-allylhydroxylamine hydrochloride there is obtained 2',4'-dichloro-2-(3-pyridyl)-acetophenone O-allyl oxime as a colourless oil.

Example 2

3 g of 2'-chloro-2-(2-pyrazinyl)-acetophenone and 0.8 g of O-methylhydroxylamine hydrochloride are dissolved in 10 ml of pyridine and the mixture is heated at 80° for 30 minutes. The pyridine is then removed under reduced pressure and water is added to the crude product. Thereupon, the mixture is extracted with ethyl acetate and the organic phase is dried over sodium sulfate and concentrated to yield 2'-chloro-2-(2-pyrazinyl)-acetophenone O-methyl oxime as an oil.

In an analogous manner,
from 4'-fluoro-2-(2-pyrazinyl)-acetophenone and O-methylhydroxylamine hydrochloride there is obtained 4'-fluoro-2-(2-pyrazinyl)-acetophenone O-methyl oxime, m.p. 52°–54°;
from 4'-bromo-2-(2-pyrazinyl)-acetophenone and O-methylhydroxylamine hydrochloride there is obtained 4'-bromo-2-(2-pyrazinyl)-acetophenone O-methyl oxime, m.p. 81°–84°;
from 4'-chloro-2-(2-pyrazinyl)-propiophenone and O-methylhydroxylamine hydrochloride there is obtained 4'-chloro-2-(2-pyrazinyl)-propiophenone O-methyl oxime as an oil;
from 2',4'-dichloro-2-(2-pyrazinyl)-acetophenone and O-methylhydroxylamine hydrochloride there is obtained 2',4'-dichloro-2-(2-pyrazinyl)-acetophenone O-methyl oxime as an oil;
from 2',4'-dichloro-2-(2-pyrazinyl)-acetophenone and O-ethylhydroxylamine hydrochloride there is obtained 2',4'-dichloro-2-(2-pyrazinyl)-acetophenone O-ethyl oxime as an oil;
from 2',4'-dichloro-2-(2-pyrazinyl)-acetophenone and O-allylhydroxylamine hydrochloride there is obtained 2',4'-dichloro-2-(2-pyrazinyl)-acetophenone O-allyl oxime as an oil;
from 2',4'-dichloro-2-(2-pyrazinyl)-propiophenone and O-methylhydroxylamine hydrochloride there is obtained 2',4'-dichloro-2-(2-pyrazinyl)-propiophenone O-methyl oxime as an oil.

Example 3

A solution of 3 g of 2',4'-dichloro-2-(3-pyridyl)-acetophenone oxime in 25 ml of dimethoxyethane is treated portionwise with 0.51 g of sodium hydride dispersion (55% in oil) and the mixture is stirred for 30 minutes at room temperature. Thereupon, 2.0 g of ethyl iodide are added and the mixture is heated at reflux temperature. After 4 hours, the mixture is poured onto ice and extracted with ethyl acetate. The organic phase is dried over sodium sulfate and concentrated under reduced pressure. The crude product is purified by chromatography on silica gel to yield 2',4'-dichloro-2-(3-pyridyl)-acetophenone O-ethyl oxime as a yellowish oil.

In an analogous manner,
from 2',4'-dichloro-2-(3-pyridyl)-acetophenone oxime and isopropyl bromide there is obtained 2',4'-dichloro-2-(3-pyridyl)-acetophenone O-isopropyl oxime as a yellowish oil;
from 2',4'-dichloro-2-(3-pyridyl)-acetophenone oxime and propargyl bromide there is obtained 2',4'-dichloro-2-(3-pyridyl)-acetophenone O-propargyl oxime, m.p. 60°–62°;
from 4'-chloro-2-(2-pyrazinyl)-acetophenone oxime and propargyl bromide there is obtained 4'-chloro-2-(2-pyrazinyl)-acetophenone O-propargyl oxime, m.p. 76°–77°;
from 2',4'-dichloro-2-(2-pyrazinyl)-acetophenone oxime and propargyl bromide there is obtained 2',4'-dichloro-2-(2-pyrazinyl)-acetophenone O-propargyl oxime as an oil.

II. PREPARATION OF THE STARTING MATERIALS

Example 4

The 2',4'-dichloro-2-(3-pyridyl)-acetophenone required as the starting material in Example 1 can be prepared as follows:

A mixture of 27.6 g of ethyl 2,4-dichlorobenzoate and 20.81 g of ethyl 3-pyridylacetate at 20°–25° is treated portionwise with 10.59 g of sodium methoxide. The mixture is subsequently heated at 65°–70° and resulting readily volatile products are blown off with dry nitrogen. After 20 hours, the mixture is treated with 40 ml of concentrated hydrochloric acid and heated at reflux temperature for 18 hours. The mixture is washed with diethyl ether and the aqueous phase is made basic by adding concentrated ammonia and extracted with methylene chloride. The organic phase is concentrated and the crude product is chromatographed on silica gel with methylene chloride/methanol (98:2) to yield 2',4'-dichloro-2-(3-pyridyl)-acetophenone, which can be crystallized from diethyl ether/n-pentane and melts at 55°–56°.

Example 5

The 2',4'-dichloro-2-(2-pyrazinyl)-acetophenone required as the starting material in Example 2 can be prepared as follows:

20 g of 2-methylpyrazine are added dropwise to a suspension of sodium amide in liquid ammonia (from 200 ml of ammonia and 4.83 g of sodium) at −30° and the mixture is allowed to stir for 30 minutes. 20.5 g of methyl 2,4-dichlorobenzoate are then slowly added dropwise and the mixture is reacted at −30° for 1 hour. Then the mixture is treated with ammonium chloride, ammonia is driven off and diethyl ether is added. The organic phase is washed with water, dried over sodium sulfate and concentrated. After treatment with a small amount of ethanol, 2',4'-dichloro-2-(2-pyrazinyl)-acetophenone crystallizes out from the crude reaction product. The product melts at 96°–98°.

In an analogous manner, from 2-methylpyrazine and methyl 2-chlorobenzoate there is obtained 2'-chloro-2-(2-pyrazinyl)-acetophenone as an oil;

from 2-methylpyrazine and methyl 4-fluorobenzoate there is obtained 4'-fluoro-2-(2-pyrazinyl)-acetophenone, m.p. 100°–103°;

from 2-methylpyrazine and methyl 4-bromobenzoate there is obtained 4'-bromo-2-(2-pyrazinyl)-acetophenone, m.p. 121°–122°;

from 2-ethylpyrazine and methyl 4-chlorobenzoate there is obtained 4'-chloro-2-(2-pyrazinyl)-propiophenone, m.p. 85°;

from 2-ethylpyrazine and methyl 2,4-dichlorobenzoate there is obtained 2',4'-dichloro-2-(2-pyrazinyl)-propiophenone as an oil.

Example 6

The 4'-chloro-2-(2-pyrazinyl)-acetophenone oxime required as the starting material in Example 3 can be prepared as follows:

10 g of 4'-chloro-2-(2-pyrazinyl)-acetophenone, 10 g of hydroxylamine hydrochloride and 12 g of anhydrous sodium carbonate are stirred at 60° in 100 ml of ethanol for 2 hours. The mixture is then treated with water and extracted with ethyl acetate, and the organic phase is dried over sodium sulfate and subsequently concentrated. The residue is crystallized from acetone/n-hexane to yield 4'-chloro-2-(2-pyrazinyl)-acetophenone oxime, m.p. 134°.

In an analogous manner, from 2',4'-dichloro-2-(2-pyrazinyl)-acetophenone and hydroxylamine hydrochloride there is obtained 2',4'-dichloro-2-(2-pyrazinyl)-acetophenone oxime as a viscous oil;

from 2',4'-dichloro-2-(3-pyridyl)-acetophenone and hydroxylamine hydrochloride there is obtained 2',4'-dichloro-2-(3-pyridyl)-acetophenone oxime, m.p. 134°–136°.

III. FORMULATION EXAMPLES

Example 7

(a) Spray powder for active substances which are liquid or which melt below 75°.

|  | Parts by weight |
|---|---|
| Active substance of formula I | 50 |
| Hydrated silicic acid | 37 |
| Kaolin | 5 |
| Alkylphenol ethoxylate | 4 |
| Sodium polynaphthalenesulphonate | 4 |
|  | 100 |

The liquid or molten active ingredient is absorbed onto the silicic acid, the remaining components are admixed and the mixture is finely ground in a suitable mill.

(b) Spray powder for solid active substances which melt above 75°.

|  | Parts by weight |
|---|---|
| Active substance of formula I | 50 |
| Hydrated silicic acid | 5 |
| Kaolin | 42 |
| Sodium lauryl sulphate | 1 |
| Sodium lignosulphonate | 2 |
|  | 100 |

The components are mixed with one another and the mixture is finely ground in a suitable mill.

Example 8

Emulsifiable concentrate for active substances which are liquid at 20°–25°.

|  | Parts by weight |
|---|---|
| Active substance of formula I | 500 |
| Castor oil ethoxylate | 100 |
| Calcium dodecylbenzene sulphonate | 25 |
| Mixture of C$_{10}$—alkylbenzenes ad | 1000 parts by volume. |

The components are mixed with one another until a clear solution results.

I claim:

1. A compound of the formula

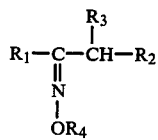

wherein $R_1$ is 2-halo-, 4-halo-, or 2,4-dihalophenyl, $R_2$ is 3-pyridyl or 2-pyrazinyl, $R_3$ is hydrogen or straight-chain $C_{1-4}$-alkyl, and $R_4$ is $C_{1-6}$-alkyl, $C_{3-6}$-cycloalkyl, $C_{3-6}$-alkenyl or $C_{3-6}$-alkynyl and acid addition salts thereof.

2. The compound according to claim 1, wherein $R_1$ is 4-chlorophenyl or 2,4-dichlorophenyl.

3. The compound according to claim 1 or claim 2, wherein $R_3$ is hydrogen.

4. 2',4'-Dichloro-2-(3-pyridyl)-acetophenone O-methyl oxime.

5. A compound according to claim 1, selected from the group consisting of
4'-Chloro-2-(3-pyridyl)-acetophenone O-methyl oxime,
4'-chloro-2-(2-pyrazinyl)-acetophenone O-methyl oxime,
4'-chloro-2-(2-pyrazinyl)-acetophenone O-ethyl oxime,
4'-chloro-2-(2-pyrazinyl)-acetophenone O-allyl oxime,
2',4'-dichloro-2-(3-pyridyl)-acetophenone O-ethyl oxime,
2',4'-dichloro-2-(3-pyridyl)-acetophenone O-isopropyl oxime and
2',4'-dichloro-2-(3-pyridyl)-acetophenone O-propargyl oxime.

6. A compound according to claim 1, selected from the group consisting of
2',4'-Dichloro-2-(3-pyridyl)-acetophenone O-allyl oxime,
2'-chloro-2-(2-pyrazinyl)-acetophenone O-methyl oxime,
4'-fluoro-2-(2-pyrazinyl)-acetophenone O-methyl oxime,
4'-bromo-2-(2-pyrazinyl)-acetophenone O-methyl oxime,
4'-chloro-2-(2-pyrazinyl)-propiophenone O-methyl oxime,
2',4'-dichloro-2-(2-pyrazinyl)-acetophenone O-methyl oxime,
2',4'-dichloro-2-(2-pyrazinyl)-acetophenone O-ethyl oxime,
2',4'-dichloro-2-(2-pyrazinyl)-acetophenone O-allyl oxime,
2',4'-dichloro-2-(2-pyrazinyl)-propiophenone O-methyl oxime,
4'-chloro-2-(2-pyrazinyl)-acetophenone O-propargyl oxime and
2',4'-dichloro-2-(2-pyrazinyl)-acetophenone O-propargyl oxime.

7. A fungicidal composition which comprises a compatible inert carrier material and, as the active ingredient, an amount which is effective as a fungicide of at least one compound of the formula

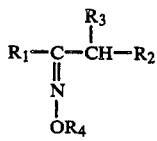

wherein $R_1$ is 2-halo-, 4-halo- or 2,4-dihalophenyl, $R_2$ is 3-pyridyl or 2-pyrazinyl, $R_3$ is hydrogen or straight-chain $C_{1-4}$-alkyl, and $R_4$ is $C_{1-6}$-alkyl, $C_{3-6}$-cycloalkyl, $C_{3-6}$-alkenyl or $C_{3-6}$-alkynyl, or an acid addition salt thereof.

8. The fungicidal composition of claim 7, wherein the active ingredient is 2',4'-dichloro-2-(3-pyridyl)-acetophenone O-methyl oxime.

9. A method for combating fungi in agriculture and in horticulture which method comprises treating the locus or goods to be protected with a fungicidally effective composition of claim 7.

10. The method of claim 9 wherein the active ingredient of the composition is 2',4'-dichloro-2-(3-pyridyl)-acetophenone O-methyl oxime.

* * * * *